(12) United States Patent
Thiagarajan et al.

(10) Patent No.: US 10,366,791 B1
(45) Date of Patent: Jul. 30, 2019

(54) METHOD AND SYSTEM FOR GLOBAL EPIDEMIC DISEASE OUTBREAK PREDICTION

(71) Applicant: EMC Corporation, Hopkinton, MA (US)

(72) Inventors: Senthil Kumar Thiagarajan, Bangalore (IN); Viyoma Sachdeva, Bangalore (IN); Sankara Narayanan, Bangalore (IN); Shikhar Pandey, Bangalore (IN)

(73) Assignee: EMC IP Holding Company LLC, Hopkinton, MA (US)

( * ) Notice: Subject to any disclaimer, the term of this patent is extended or adjusted under 35 U.S.C. 154(b) by 1102 days.

(21) Appl. No.: 14/231,148

(22) Filed: Mar. 31, 2014

(51) Int. Cl.
  *G16H 50/20* (2018.01)
(52) U.S. Cl.
  CPC .................... *G16H 50/20* (2018.01)
(58) Field of Classification Search
  CPC ...................................... G06F 19/345
  USPC ............................................... 703/2
  See application file for complete search history.

(56) References Cited

U.S. PATENT DOCUMENTS

| | | | | |
|---|---|---|---|---|
| 7,249,006 B2 * | 7/2007 | Lombardo | ............. | G16H 10/60 703/2 |
| 7,266,484 B2 * | 9/2007 | Lombardo | ............. | G16H 50/80 703/11 |
| 7,426,557 B2 * | 9/2008 | Gruhl | ............. | G06Q 50/01 709/223 |
| 9,141,762 B2 * | 9/2015 | Lev | ............. | H04M 3/42357 |
| 2003/0204130 A1 * | 10/2003 | Colston, Jr. | ............. | A61B 5/002 600/300 |
| 2007/0229290 A1 * | 10/2007 | Kahn | ............. | G16H 50/80 340/573.4 |
| 2010/0179835 A1 * | 7/2010 | Wager | ............. | G06Q 10/10 705/3 |
| 2010/0198755 A1 * | 8/2010 | Soll | ............. | G06F 19/322 706/11 |
| 2010/0316196 A1 * | 12/2010 | Jokinen | ............. | G08B 27/006 379/38 |
| 2011/0066002 A1 * | 3/2011 | Clawson | ............. | H04M 11/04 600/300 |
| 2011/0099031 A1 * | 4/2011 | Nair | ............. | G06Q 50/24 705/3 |
| 2012/0112883 A1 * | 5/2012 | Wallace | ............. | G06Q 50/22 340/10.1 |
| 2012/0183128 A1 * | 7/2012 | Clawson | ............. | G06F 19/30 379/45 |

(Continued)

OTHER PUBLICATIONS

Hogg_1997 (Introduction to Mathematical Statistics, 5th Edition, Prentice-Hall, Inc., 1995).*

(Continued)

*Primary Examiner* — Brian S Cook
(74) *Attorney, Agent, or Firm* — Ryan, Mason & Lewis, LLP

(57) ABSTRACT

Example embodiments of the present invention relate to a method, a system, and a computer program product for disease outbreak prediction analytics. The method includes calculating a respective correlation value for each outbreak attribute pair among a set of outbreak attributes for a data set regarding a disease and assigning a weight value for each outbreak attribute according to the correlation values. A risk value for the disease then may be determined according to the weight values.

20 Claims, 14 Drawing Sheets

(56) References Cited

U.S. PATENT DOCUMENTS

2012/0244886 A1* 9/2012 Blom ................. G08B 27/005
                                                  455/456.3

OTHER PUBLICATIONS

Christensen_1992 (Introduction to Statistics: A calculus based approach, Harcourt Brace Javonovich, Inc. 1992).*
Chen_2012 (Chapter 2: Use of Percentiles and Z-Scores in Anthropometry, Handbook of Anthropometry: Physical Measures of Human Form in Health and Disease, Springer Science + Business Media, LLC 2012).*
Gorunescu_2011 (Data Mining: Concepts, Models and Techniques, Springer 2011).*
Health_Perspectives_2012 (Using Social Media to Predict and Track Disease Outbreaks, Environmental Health Perspectives vol. 120 No. 1 Jan. 2012.*
Konkel_2013 (Predictive analytics allows feds to track outbreaks in real time Jan. 25, 2013 downloaded from https://fcw.com/articles/2013/01/25/flu-social-media.aspx) teaches to use social media for epidemic predictions.*
Tucker_1997 (Tucker, Exploratory Factor Analysis, 1997).*
Myers_2000 (Forecasting Disease Risk for Increased Epidemic Preparedness in Public Health, Europe PMC Funders Group, PMC Oct. 19, 2011, Adv Parasitol. 2000; 27: 309-330).*
Woolhouse_2011 (How to Make Predictions about future infectious disease risks, Phil. Trans. R. Soc. (2011) 366, 2045-2054).*
Que_2011 (Rank-based spatial clustering: an algorithm for rapid outbreak detection, J Am Med Inform Assoc 2011; 18:218-224).*

* cited by examiner

US 10,366,791 B1

METHOD AND SYSTEM FOR GLOBAL EPIDEMIC DISEASE OUTBREAK PREDICTION

A portion of the disclosure of this patent document may contain command formats and other computer language listings, all of which are subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

TECHNICAL FIELD

This application relates to context-aware disease outbreak prediction analytics.

BACKGROUND

Prediction of disease outbreaks, or disease forecasting, provides warning that a certain amount of disease may occur at a particular time in the future. The "amount of disease" may be qualitative (e.g., there will be a lot of disease) or quantitative (e.g., 35% will be infected). Prediction of disease occurrence ensures that control measures, especially the application of chemical treatments or biological control agents, are used more effectively.

SUMMARY

Example embodiments of the present invention relate to a method, a system, and a computer program product for disease outbreak prediction analytics. The method includes calculating a respective correlation value for each outbreak attribute pair among a set of outbreak attributes for a data set regarding a disease and assigning a weight value for each outbreak attribute according to the correlation values. A risk value for the disease then may be determined according to the weight values.

BRIEF DESCRIPTION OF THE DRAWINGS

The above and further advantages of the present invention may be better under stood by referring to the following description taken into conjunction with the accompanying drawings in which.

DETAILED DESCRIPTION

Figure 1:
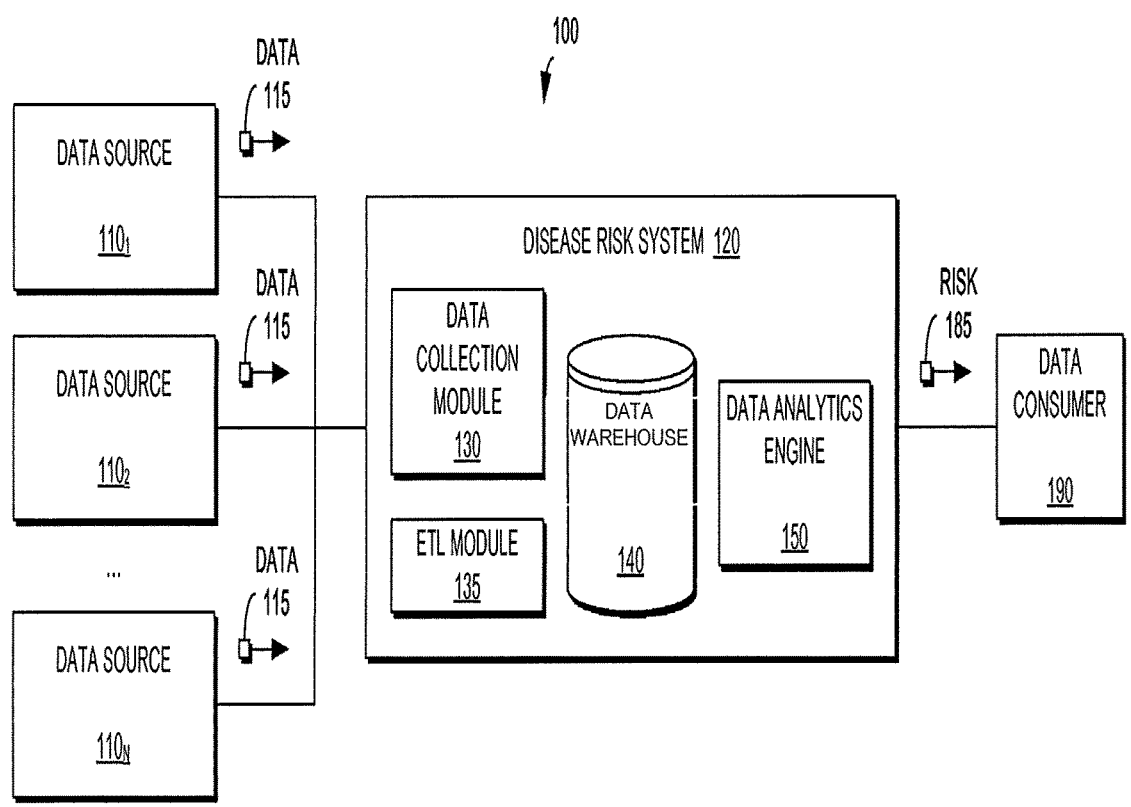
FIG. 1 is a block diagram of a system according to an example embodiment of the present invention.

Example embodiments of the present invention provide a method, a system, and a computer program product to predict global epidemic disease outbreaks for a given location and time. Example embodiments of the present invention also may perform real time analytics on reported disease outbreaks based on a user's search criteria to provide expected, personalized, and context aware outbreak information with intelligent guidance on the recommended precautionary measure and health care guidance. The user may be a nomadic user as described in U.S. patent application Ser. No. 14/040,052 entitled "ENTITY LOCATION TRACEABILITY AND PREDICTION" filed on Sep. 27, 2013 commonly assigned with the present application to EMC Corporation of Hopkinton, Mass. and incorporated herein by reference in its entirety.

Accordingly, example embodiments of the present invention may provide a methodology to predict the potential disease outbreaks for any given location across the globe for a given time period, a methodology to perform real-time analytics for context aware and personalized predictions for the nomadic user and accompanying party members (i.e., family or friends), a methodology to dynamically assign weightage and sort the outbreak information in terms of severity and to group by associated user's personal context, systems and methods for providing real-time intelligent guidance/recommendation on the required precautionary measures to handle to expected medical conditions, and location aware recommendations on the nearby medical care centers which are in alignment with the predicted or confirmed outbreaks in context to any user specific considerations from the past medical conditions/health care providers subscribed.

Example embodiments of the present invention may be of interest to the pharmaceutical industry, insurance companies, and government health regulatory bodies. Further, example embodiments of the present invention may be of interest to travel booking companies and corporate companies for their nomadic employees.

Such organizations may provide example embodiments of the present invention as a Software-as-a-Service (SaaS) offering to which subscribers may subscribe. For example, the services may be offered as a full version with all capabilities and features where the subscribers can share their employees/customers profile and health history. Alternatively, customers can also get a limited version of this solution base on their business requirements. In other words, consumers can opt in for the required services and may be charged for the set of services they have opted for. Additionally, an enterprise license may be offered with multi-channel access options which include mobile devices, web, and email/text notifications.

Such organizations also may provide example embodiments of the present invention as a Platform-as-a-Service (PaaS). For example, example embodiments of the present invention may enable options for a consumer to perform their own analytics on federated data sources. Alternatively, a hybrid model may allow access to on premise data for user profile and health history information.

Implementation of the proposed model demands larger storage for storing the outbreak history information and other related data, and it's expected to increase in multiple folds every year which gives the potential opportunity to use the products like Isilon® or VMAX® from EMC Corporation of Hopkinton, Mass. on premise for the customer or over the cloud for a SaaS model. An architecture for example embodiments of the present invention also may include RSA® authentication and authorization services for enabling access to personalized health alerts and ensure industry standards like Health Insurance Portability and Accountability Act (HIPAA) requirements, SMARTS® storage management software, and Documentum® content management software all from EMC Corporation of Hopkinton, Mass.; vSphere virtualization platform and Socialcast crowd sourcing and collaboration software by VMware of Palo Alto, Calif.; Vblock converged infrastructure systems by VCE of Richardson, Tex.; and Pivotal HD predictive analytics and data processing software by Pivotal Software, Inc. of Palo Alto, Calif.

FIG. 1 is a block diagram of a system 100 according to an example embodiment of the present invention. As illustrated in FIG. 1, a disease risk system 120 may include a data collection module 130, a data warehouse 140, and a data analytics engine 150. The data collection module 130 may collect (i.e., capture) data 115 from a plurality of data sources $110_1$-$110_N$ (110 generally). The plurality of data sources may include, but is not limited to, office and/or personal electronic calendar data, social media data (e.g., Twitter, Facebook, LinkedIn, Google Talk, etc.), mobile device data (e.g., a mobile signal indicating global positioning system (GPS) location data of cellular phone and cellular phone identifier), travel data (e.g., booking, check-in, boarding information regarding flight, cruise, bus, railways and/or hotel), monetary transaction data (e.g., automatic teller machine (ATM) withdrawal data such as location of ATM where withdrawal occurred), purchase data (e.g., credit card swipe information such as location of point of sale), alerts from the health sector (e.g., public/private health organizations/bodies), alerts from private organizations (e.g., hospitals and non-government organizations), analytics sources (e.g., Google Analytics), news agencies, user contributions, crowd polling, user profile information, user health history information (if available), and weather data from public/private source (e.g., present and forecasted conditions). Such data is collectively an example of "activity-related data." The data 115 may be collected from various systems and devices (e.g., public and private) that are operatively coupled to the data collection module 130. The data can be pulled from the data sources 110 and/or pushed by the data sources 110.

The data collection module 130 is operatively coupled to an Extract, Transform, and Load (ETL) module 135. As is known, ETL is a process in data warehousing wherein data is extracted from one or more outside data sources, transformed to fit operational needs (e.g., quality of service levels) and/or storage formats, and loaded into a target data warehouse 140. Thus, in this embodiment, the ETL module 135 extracts data collected by the data collection module 130, transforms it to a given format and/or operational need, and then loads it into the data warehouse 140.

A data analytics engine 150 is operatively coupled to the data warehouse 140. The data analytics engine 150 analyzes all or portions of the data stored in the data warehouse 140, as will be explained in detail below, and provides a disease risk prediction result 185 regarding one or more subject entities to a user or other system (consumer or requestor) 190.

Figure 2:
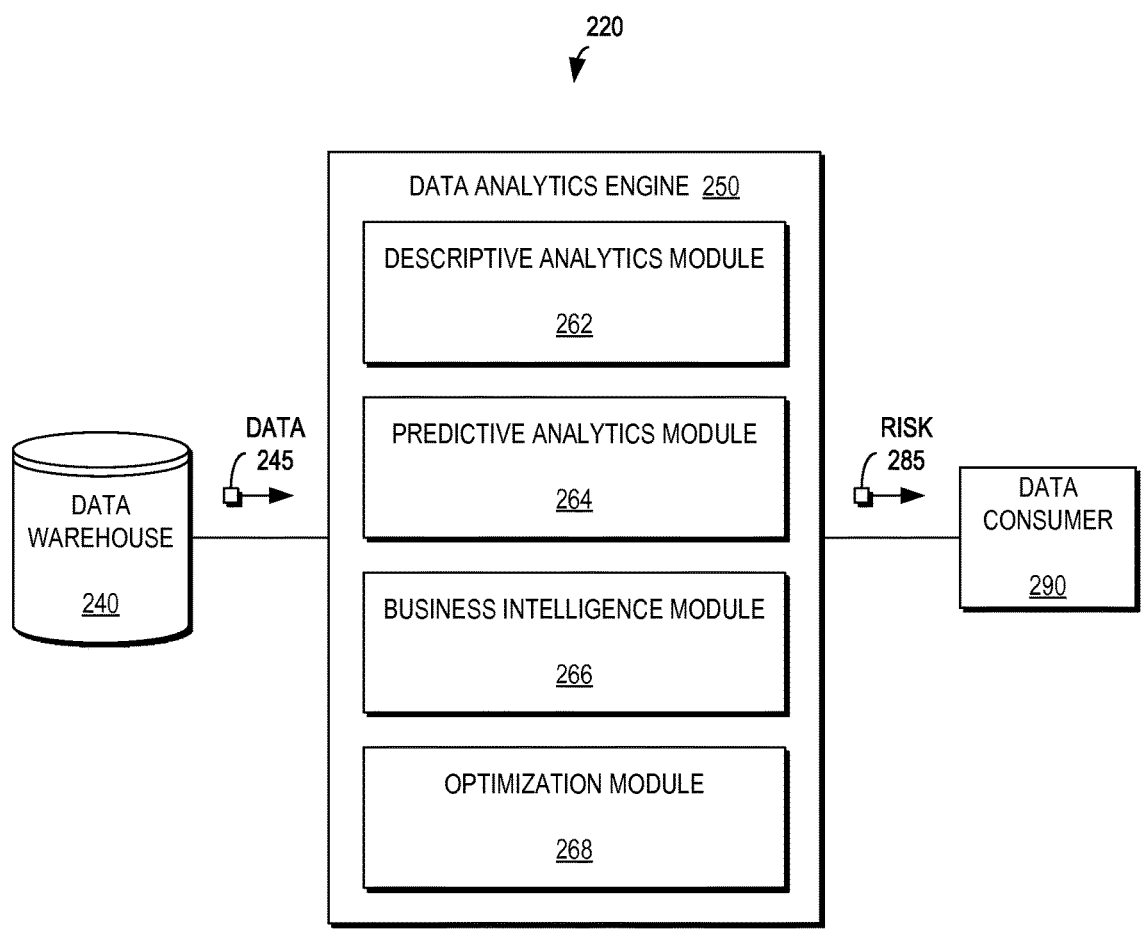
FIG. 2 is a block diagram of a data analytics engine according to an example embodiment of the present invention.

FIG. 2 is a block diagram of a data analytics engine 250 according to an example embodiment of the present invention. As illustrated in FIG. 2, the data analytics engine 250 may include a descriptive analytics module 262, a predictive analytics module 264, a business intelligence module 266, and an optimization module 268. These modules 262-268 are examples of processing modules associated with an analytics function which, in general, attempts to obtain new insights and understanding of performance of an operation based on data and statistical methods. In this case, the analytics function is a disease outbreak prediction function with respect to a subject entity.

The descriptive analytics module 262 may analyze the data 245 from the data warehouse 240 and obtain descriptive information about the data. For example, this includes quantitatively describing the main features of a collection of data. This descriptive information may be used by the predictive analytics module 264 to execute a prediction algorithm, as will be described in greater detail below, along with the business intelligence module 266, which may be used to provide business related metrics, when needed or preferred, that yield information about the subject entity's activities (in the context of a business scenario). Thus, the descriptive analytics answers, for example, the question of "who" and "where" in a past or present context from historical data, while the predictive analytics answers the question, for example, "what disease will break out in the future." However, it can also predict what diseases are likely to have outbreaks currently if that is not known from existing data. The optimization module 268 may assist in selecting the optimal disease prediction data, as will be described in greater detail below.

Although the components 110 through 190 are shown as separate in FIG. 1, these components or portions thereof may be implemented at least in part on a common processing platform. In other embodiments, components 110 through 190 may each be implemented on a separate processing platform. It is also to be understood that a given embodiment may include multiple instances of the components 110 through 190, although only single instances of such components are shown in the system diagram for clarity and simplicity of illustration.

FIGS. 3-12 illustrate methods according to respective example embodiments of the present invention for determining risk values associated with disease outbreaks.

Figure 3:
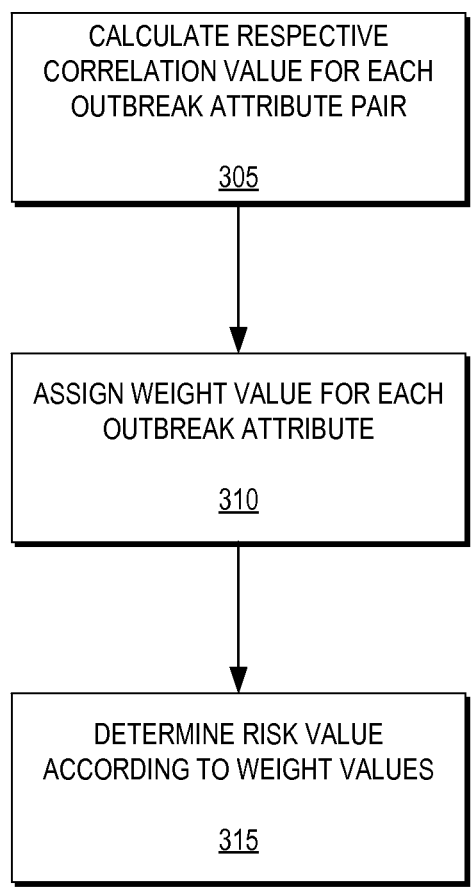
FIGS. 3-12 are flow diagrams according to respective example embodiments of the present invention.

FIG. 3 is a flow diagram of a method according to an example embodiment of the present invention. As illustrated in FIG. 3, the method includes calculating a respective correlation value for each outbreak attribute pair among a set of outbreak attributes for a data set regarding a disease (305) and assigning a weight value for each outbreak attribute according to the correlation values (310). The method further includes determining a risk value for the disease according to the weight values (315).

For example, a prediction algorithm for medical surveillance may be comprised of three phases: correlation, weighting, and standardizing. In the correlation phase, as described in greater detail below, a correlation matrix may be generated to allot a correlation value "r" to each attribute for a disease. Disease attributes may include time period, location, weather conditions, event, count, and people affected. The sample correlation coefficient may be calculated as:

$$r = \frac{\sum XY - n\overline{XY}}{\sqrt{\sum X^2 - n\overline{X}^2}\sqrt{\sum Y^2 - n\overline{Y}^2}},$$

where X and Y are respective attributes of the attribute pair and n is the number of measurements.

A sample correlation matrix for historical data for a disease, such as Malaria, is provided below in Table 1.

TABLE 1

Correlation matrix for historical data for Malaria

| | Time Period | Place | Weather Condition | Event | Count | People Affected |
|---|---|---|---|---|---|---|
| Time Period | 1.00 | 0.13 | −0.11 | 0.14 | −0.04 | 0.02 |
| Place | 0.13 | 1.00 | −0.26 | 0.33 | −0.12 | −0.16 |
| Weather Condition | −0.11 | −0.26 | 1.00 | −0.06 | 0.09 | 0.03 |
| Event | 0.14 | 0.33 | −0.06 | 1.00 | 0.19 | 0.12 |
| Count | −0.04 | −0.12 | 0.09 | 0.19 | 1.00 | 0.82 |
| People Affected | 0.02 | −0.16 | 0.03 | 0.12 | 0.82 | 1.00 |

A sample correlation matrix for current data for a disease, such as Malaria, is provided below in Table 2.

TABLE 2

Correlation matrix for current data for Malaria

| | Time Period | Place | Weather Condition | Event | Count | People Affected |
|---|---|---|---|---|---|---|
| Time Period | 1.00 | 0.15 | −0.14 | −0.13 | 0.03 | 0.19 |
| Place | 0.15 | 1.00 | −0.22 | −0.04 | −0.25 | 0.40 |
| Weather Condition | −0.14 | 0.22 | 1.00 | 0.10 | 0.08 | −0.09 |
| Event | −0.13 | −0.04 | 0.10 | 1.00 | 0.20 | 0.01 |
| Count | 0.03 | −0.25 | 0.08 | 0.20 | 1.00 | 0.30 |
| People Affected | 0.19 | 0.40 | −0.09 | 0.01 | 0.30 | 1.00 |

A sample correlation matrix for current data for a disease, such as Malaria, is provided below in Table 3.

TABLE 3

Correlation matrix for personalized data for Malaria

| | Time Period | Place | Weather Condition | Event | Count | People Affected |
|---|---|---|---|---|---|---|
| Time Period | 1.00 | 0.29 | 0.05 | −0.31 | NA | NA |
| Place | 0.29 | 1.00 | −0.13 | 0.44 | NA | NA |
| Weather Condition | 0.05 | −0.13 | 1.00 | −0.10 | NA | NA |
| Event | −0.31 | 0.44 | −0.10 | 1.00 | NA | NA |
| Count | NA | NA | NA | NA | 1.00 | NA |
| People Affected | NA | NA | NA | NA | NA | 1.00 |

In the weighting phase, the disease outbreak severity weighting may assign a weighting to each attribute depending upon the relationship between the mean "r" values (e.g., historic (rHist)—the mean of all "r" values of any attribute from historic data, current (rCur)—the mean of all "r" values of any attribute from current data, and personal (rPers)—the mean of all "r" values of any attribute from personalized data).

The mean of any variable X is the summation:

$$\bar{x} = \frac{1}{N}\sum_{i=1}^{N} x_i = \frac{x_1 + x_2 + \ldots + x_N}{N},$$

where N is the number of samples taken.

Based upon the correlation value "r", a weighting may be assigned to the attributes for each disease. For example, if data is available for a plurality of diseases (e.g., Malaria, Meningococcal, Meningitis, Dengue, and Typhoid) a respective correlation matrix may be generated for each disease illustrating correlation values between respective disease attribute pairs.

The outbreak severity weighting may be calculated according to the following. For each attribute, the sum of rHist, rCur, and rPers may be calculated and assigned a weighting. For example, for the example above for Malaria having six attributes, rHist, rCur, and rPers for Time Period may be calculated, summed, and assigned a weighting W1; rHist, rCur, and rPers for Place may be calculated, summed, and assigned a weighting W2; rHist, rCur, and rPers for Weather Condition may be calculated, summed, and assigned a weighting W3; rHist, rCur, and rPers for Event may be calculated, summed, and assigned a weighting W4; rHist, rCur, and rPers for Count may be calculated, summed, and assigned a weighting W5; and rHist, rCur, and rPers for People Affected may be calculated, summed, and assigned a weighting W6.

In certain embodiments, the correlation r values may be interpreted in ranges such that certain ranges are assigned high and low correlation attributes. These high and low correlation amounts then may be used in assigning weighting values according to the various combinations. For example, see the illustration in Table 4.

TABLE 4

Attribute correlation and weighting values

| rHist | rCur | rPers | W |
|---|---|---|---|
| H | H | H | 10 |
| H | H | L | 9 |
| H | L | H | 9 |
| H | L | L | 7 |
| L | H | H | 8 |
| L | H | L | 7 |
| L | L | H | 6 |
| L | L | L | 5 |

Therefore, for Malaria, the weight assigned to the disease may be calculated as the sum of the weights of the individual attributes:

$D1=W1+W2+W3+W4+W5+W6.$

The score standardization phase may perform standardization across a set of values (i.e., finding a common metric or scale) known as Z-scores. However, instead of translating data to a fixed range (as with percentile rescaling), Z-scores are anchored by the mean and standard deviation of the original values and rescaled such that the new mean is 0 and the new standard deviation is 1. Accordingly, the resulting Z-scores correspond to points on the standard normal curve with a theoretical range of approximately −3 to +3 (however, the actual range for each indicator will be different). It should be noted that Z-scores can be calculated for individual level or aggregate level data.

Suppose there is a list of weightings for a plurality of diseases:

$L=\{D1,D2,D3,D4,D5,\ldots\}.$

Example embodiments of the present invention may calculate the mean:

Mean$=[D1+D2+D3+D4+D5\ldots]/n,$ where n=number of values in L. Example embodiments of the present invention the calculate the standard deviation of the list L:

$$\sigma = \sqrt{\frac{1}{N}\sum_{i=1}^{N}(x_i - \bar{x})^2}.$$

Therefore, the Z-score for disease D1 is calculated as:

$$Z(D1)=[D1-\text{Mean}]/SD.$$

Application of the above calculations to each disease provides a list of Z-scores:

$$ZL=\{Z(D1),Z(D2),Z(D3),Z(D4),Z(D5)\}.$$

Example embodiments of the present invention then sort the list of Z-scores (e.g., in descending order) to determine the disease with the highest predicted chance of outbreak (i.e., the disease having the Z-score at the top of the list).

It should be understood that, in the case of a plurality of respective diseases having the same Z-score, a tie breaker may be applied, such as the first disease to be assigned that Z-score.

Figure 4:
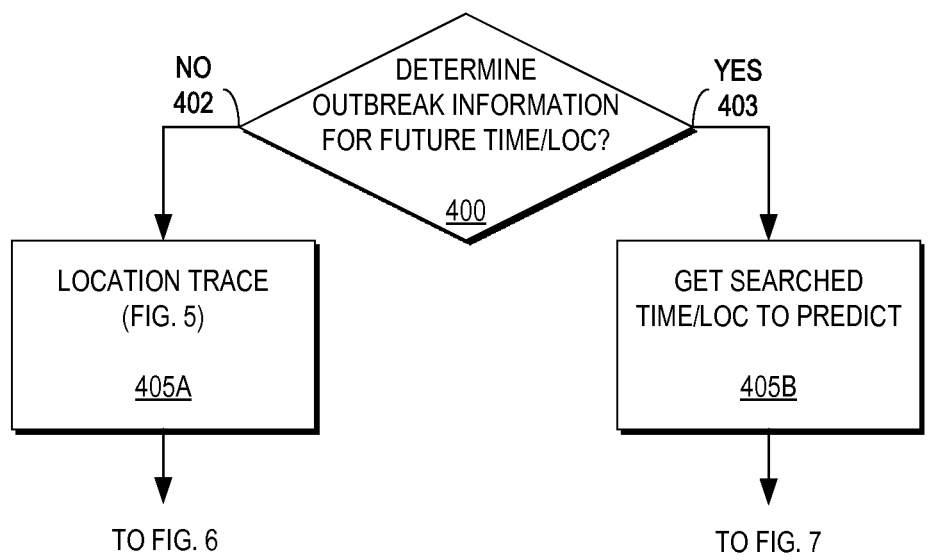

FIG. 4 is a flow diagram of a method according to an example embodiment of the present invention for determining disease outbreak information for a present time/location or a future time/location. As illustrated in FIG. 4, a user may engage methods according to example embodiments of the present invention to determine outbreak information (400). If the user is determining outbreak information for a current time/location (402), the method may perform a location trace (405A) as further illustrated in FIG. 5. The method then may continue with the method of FIG. 6. Conversely, if the user is determining outbreak information for a future time/location (403), the method may get the searched time/location to perform prediction (405B) as further illustrated in FIG. 7.

Figure 5:
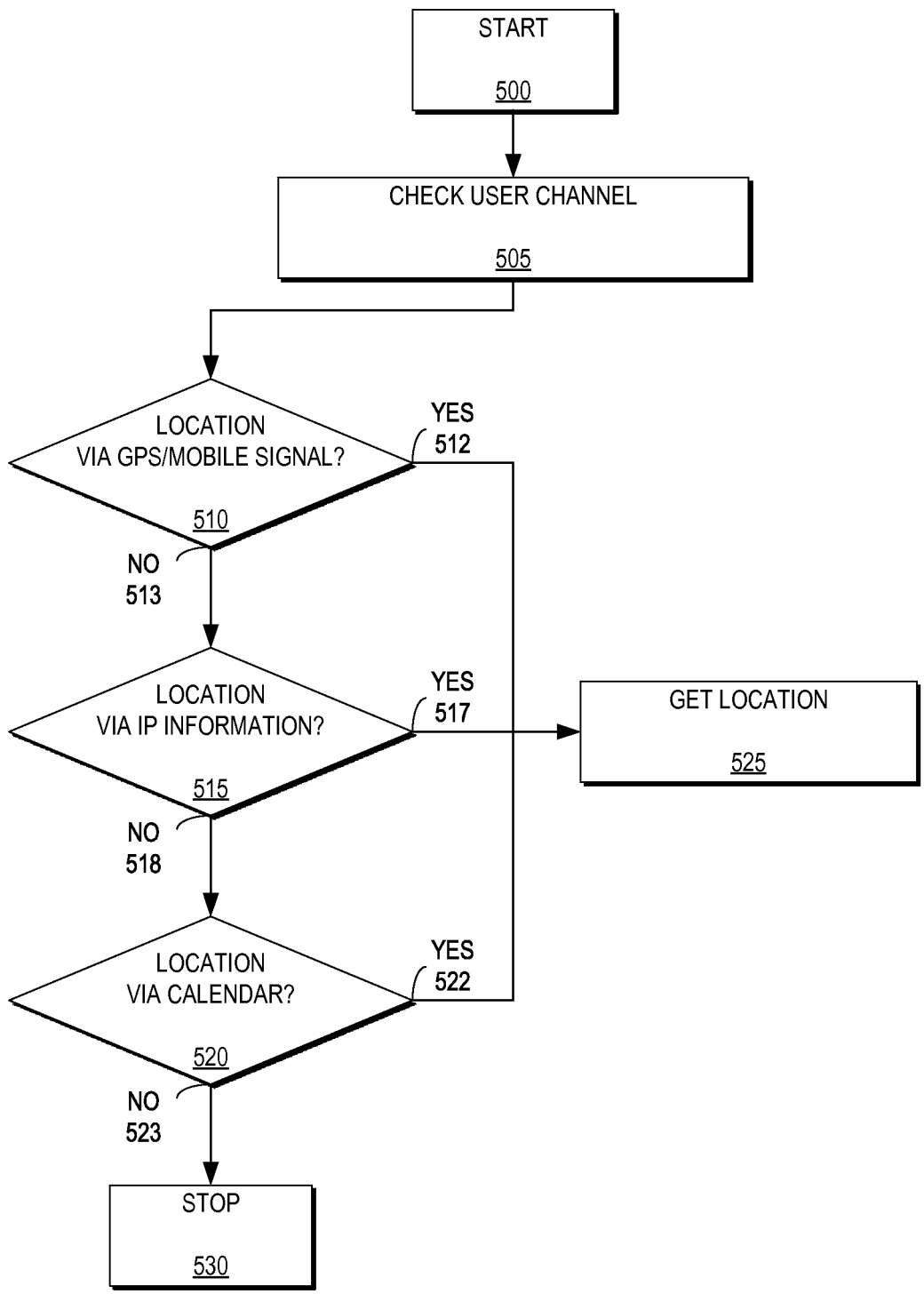

FIG. 5 is a flow diagram of a location trace (LT) method according to an example embodiment of the present invention for performing a location trace for a nomadic user. As illustrated in FIG. 5, the method may start (500) and check the user channel (505) to determine the method the user is using to connect to the system. For example, the user may use a mobile channel or a fixed location channel. The method then may determine if the user is logged in through mobile (510). If the user is mobile (512), the system may get the user's location (525) such as via available GPS or mobile signal data. If the user if not mobile (513), the system may determine whether location data is available by the user's IP address (515). If IP address information is available (517), the system may determine the user's location (525). However, if location information is not available (518), the system may determine the user's location from calendar information (520). If location information is available (522), the system may determine the user's location (525). If location information is not available, the method stops (530). As described above, example embodiments of the present invention may invoke a hierarchy of potential location data which may vary in accuracy.

Figure 6:
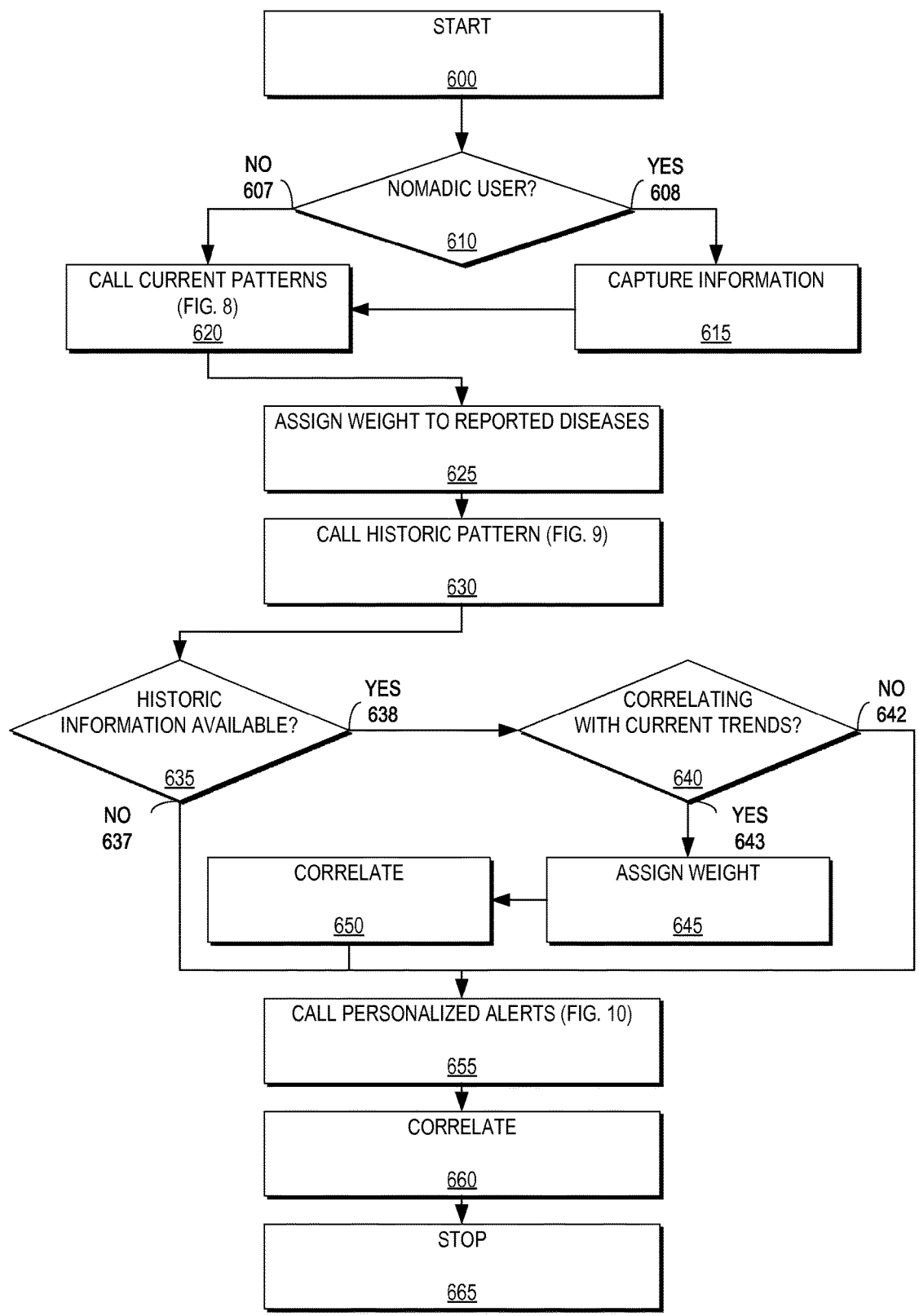

FIG. 6 is a flow diagram of a method according to an example embodiment of the present invention for calculating respective correlation values for disease outbreak attribute pairs and assigning a weight value for each outbreak attribute. As illustrated in FIG. 6, the method may start (600) and determine whether the user is a nomadic user (610), as described in the above-referenced application incorporated herein by reference. If the user is a nomadic user (608) information regarding the user's movements may be captured (615). However, if the user is not a nomadic user (607), the method may call the current patterns (CP) method as illustrated in FIG. 8 (620).

Figure 8:
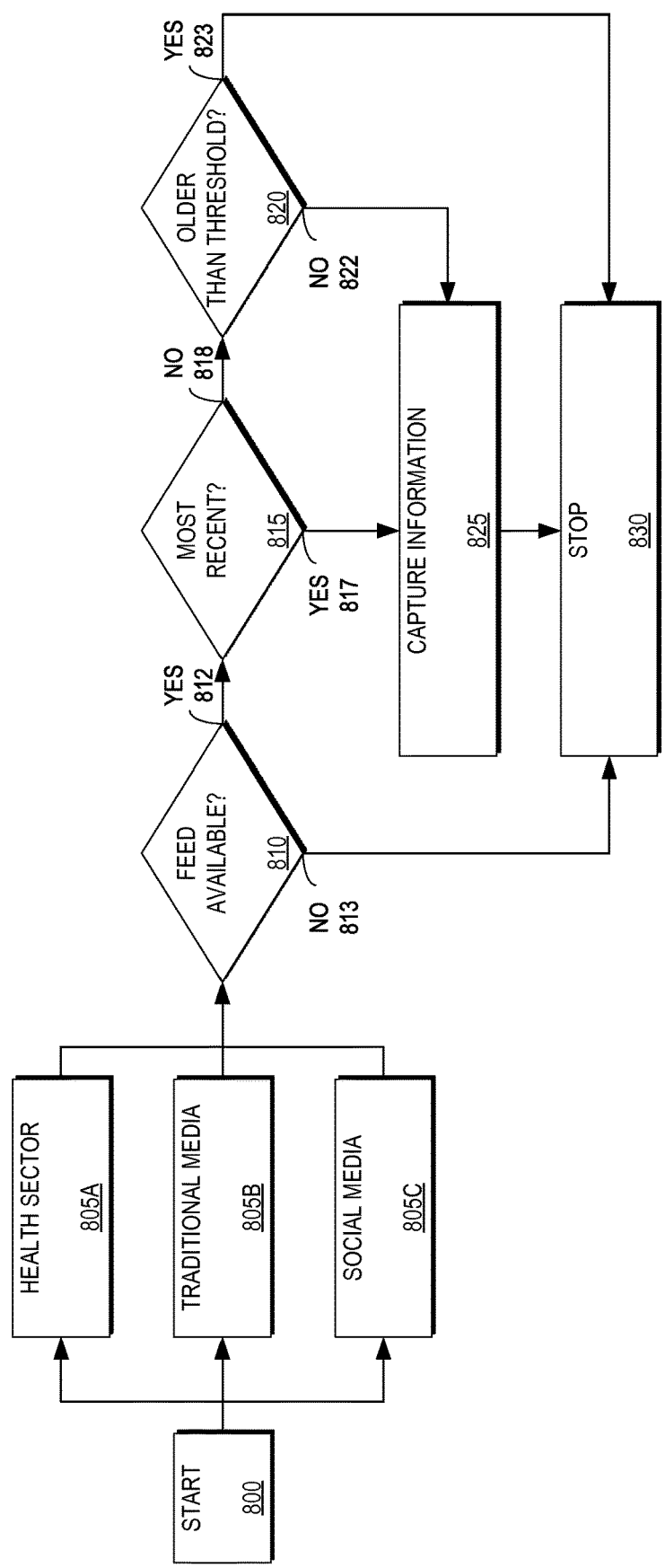

FIG. 8 is a flow diagram of a method according to an example embodiment of the present invention for calculating current disease outbreak patterns. As illustrated in FIG. 8, the method may start (800) and check various feeds/data sources for data (810). For example, the method may check the health sector (805A), such as alerts from government health bodies, for a given location in a given time period. Likewise, the method may check traditional media sources (805B), such as the private health sector and newspapers for the given location and the given time period. Similarly, the method may check social media (805C), such as crowd sourcing and social channels for the given location and given time period.

For each feed available (812), the method may determine whether the data is the most recent data (815) and, if so (817), capture the information (825). If the data is not the most recent data (818), the method may determine whether the data is older than a preset threshold for stale data (820). If the data is below the threshold (822), the method may capture the information (825). However, if the data is older than the threshold (823), the data may be considered stale and should not be considered; therefore the method stops. Likewise, if data is not available for a particular feed (813), the method stops for that feed (830).

Returning to FIG. 6, the method then may assign a weight to the reported diseases (625). For example, the weighting may be determined according to the number of diseases and the authenticity of the data sources from which data was drawn. The method then may call a historic pattern (HP) method as illustrated in FIG. 9.

Figure 9:
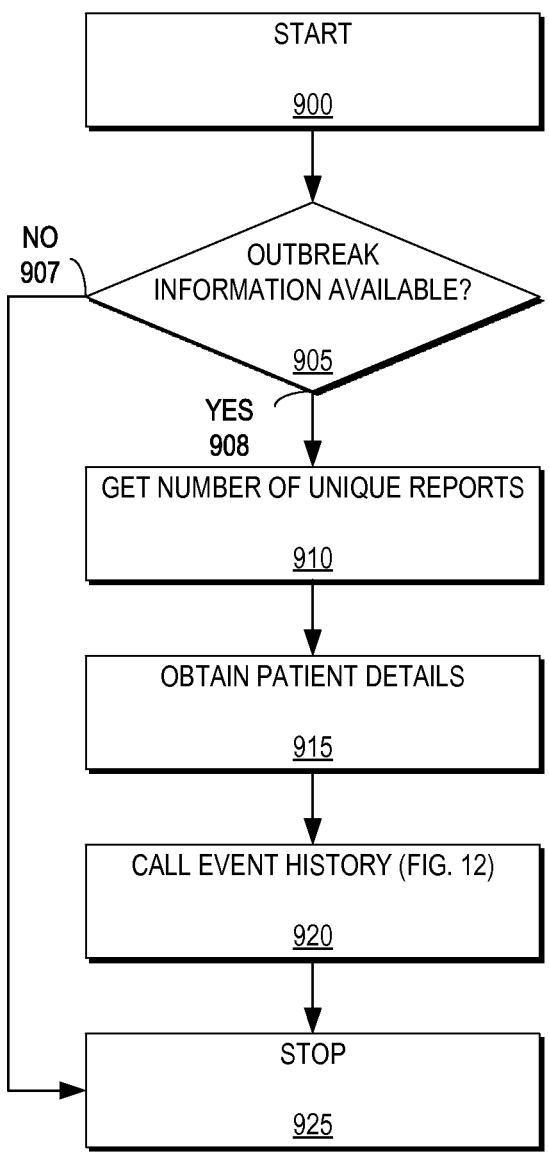
Figure 12:
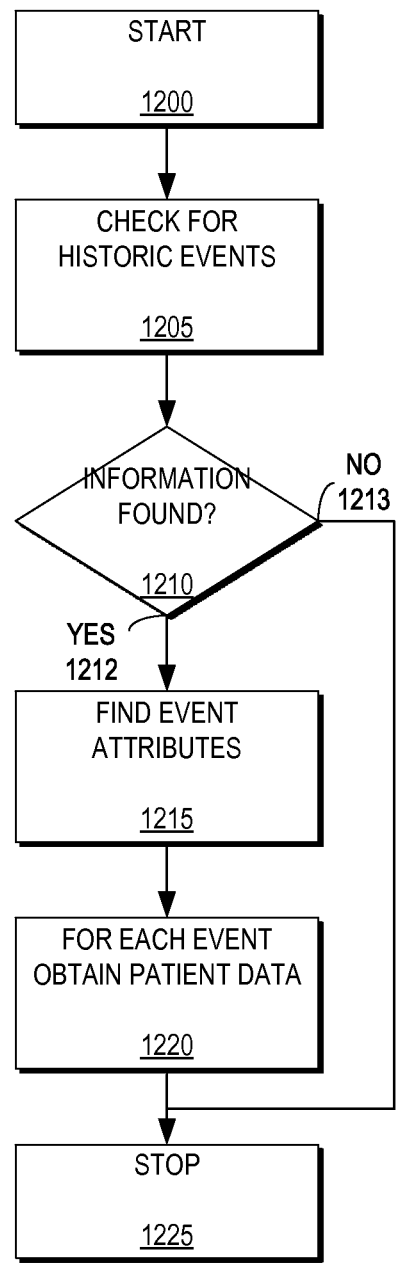

FIG. 9 is a flow diagram illustrating a method according to an example embodiment of the present invention for finding historical disease outbreaks for a given location and a given time frame. First, the method may start (900) and determine whether outbreak information for the disease is available (905). If outbreak information for a particular disease is not available (907), the method stops (925). However, if disease outbreak information for the disease is available (908), the method may gather the number of unique reports of the disease (910) and obtain patient details (915) such as gender, age, and disease type. The method then may call an event history method (920) as illustrated in FIG. 12. After calling the event history, the method stops (925).

FIG. 12 is a flow diagram of a method according to an example embodiment of the present invention for checking for historic events associated with a place and given time span. For example, as illustrated in FIG. 12, the method may start (1200) and check for historic events (1205). If historic information is found (1210) for the given place and given time span (1212), attributes regarding the event may be found (1215), such as the number of people in attendance at the event. Further, for each event found, patient data is obtained (1220), such as gender, age, and disease type. The method then may stop (1225). Likewise, if historical event information is not found (1213), the method also stops (1225).

Figure 10:
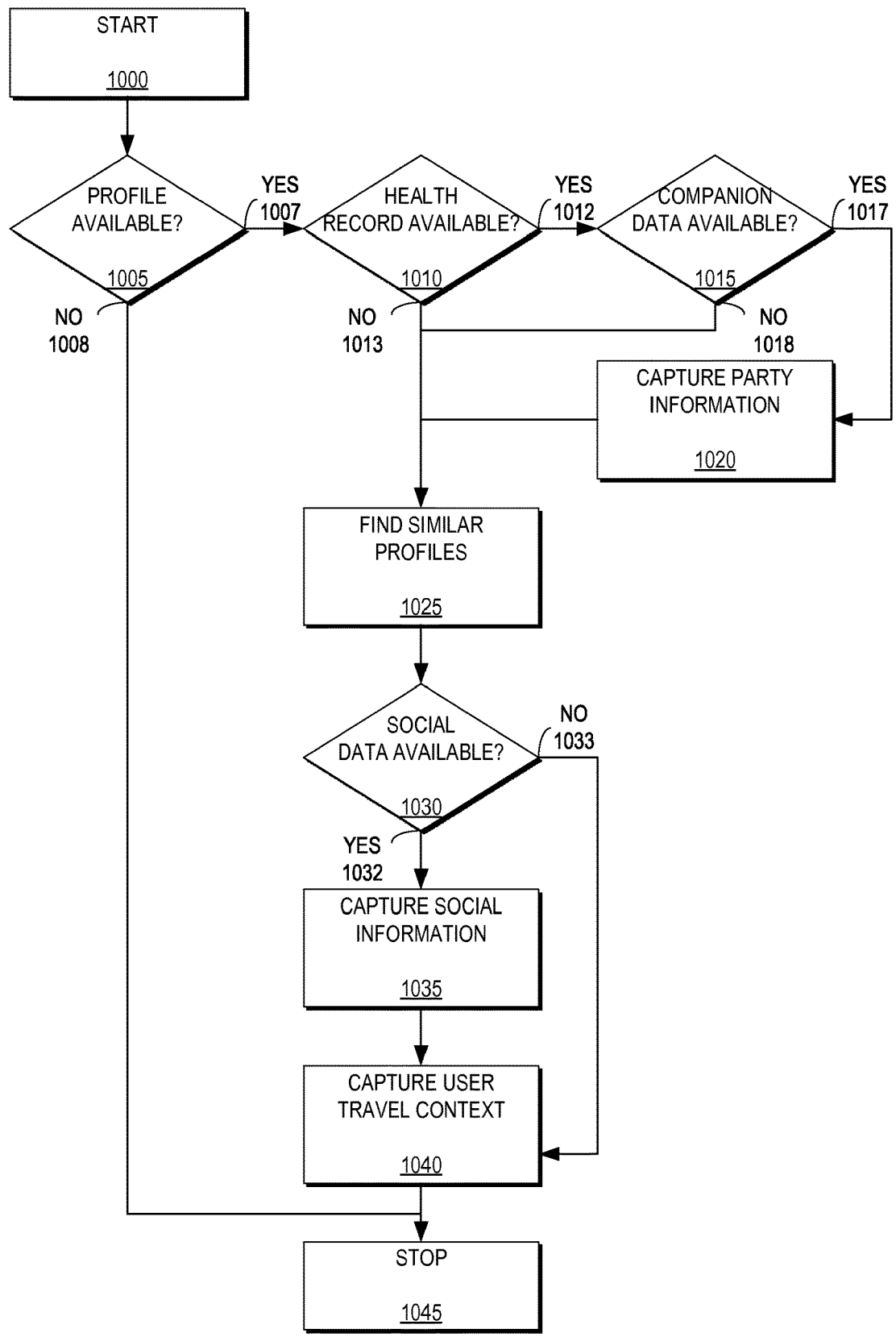

Returning to FIG. 6, the method may determine whether historic data was returned by the historic pattern call (635). If historic data was returned (638), the method then may determine whether the historic data correlates with current trend data (640). If the historic data is correlating with current trends (643), the method then may continue by assigning a weight (645) as described above and correlate the weighted historic data with weighted current trends (650). After this correlation, if there is no historic information available (637) or if the historic data is not correlating with current trends (642), the method then may call a personalized alerts (PA) method as illustrated in FIG. 10. The method then may correlated the current and historical data with the personalized trends, if available and assign a weightage (660). Then method then stops (665).

FIG. 10 is a flow diagram of a method according to an example embodiment of the present invention for determining personalized data. The method starts (1000) and determines whether user profile information is available (1005). If user profile information is available (1007), the method then determines whether the user's health record information is available (1010). Similarly, if the user has companions (i.e., is travelling with business colleagues or family/friends), the method determines whether similar information is available for the companions (1015). If companion data is available (1017), the companion information is captured from, for example, health records (1020). The method then continues (or if the user's health record is unavailable (1013) or if companion data is unavailable (1018)) to find similar matching profiles affected during the given time, if available (1025). The method also checks whether any social feed data is available (1030) and, if so (1032), captures the social information of related parties in that location (1035). The method then continues (or if social data is not available (1033)) to capture user travel context information during the given time (1040) and then stops (1045).

Figure 7:
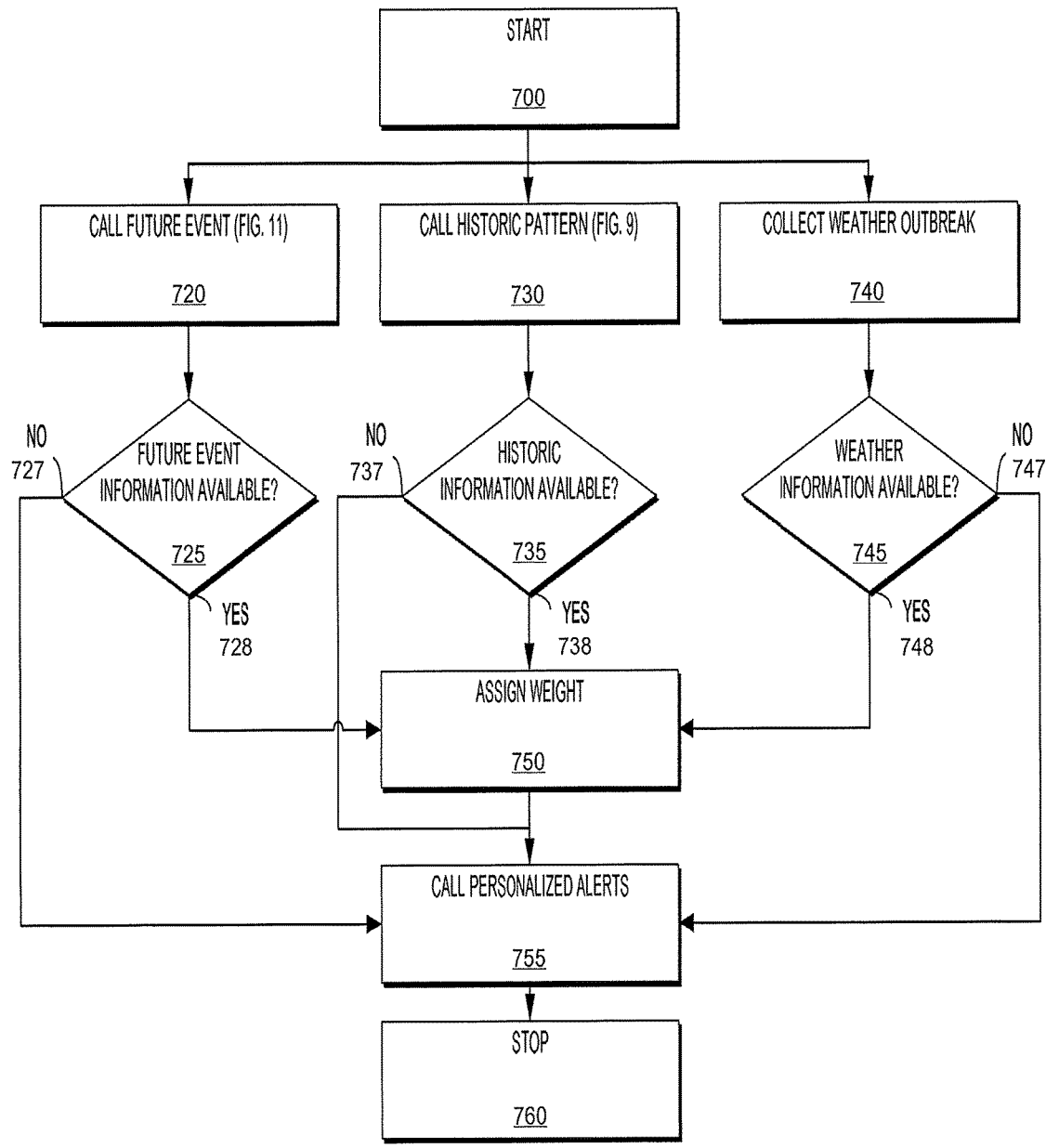

Returning to FIG. 4, if the user is using the method to determine disease outbreak data for a future time or location (403), the method gets the searched location and time to predict the disease outbreak information and then continues with the method illustrated in FIG. 7.

FIG. 7 is a flow diagram of a method according to an example embodiment of the present invention for predicting disease outbreak information for a future time/location. As illustrated in FIG. 7, the method starts (700) and includes, calling a future event (FE) method (720) as illustrated in FIG. 11, calling the historic pattern method illustrated above with respect to FIG. 9 (730), and collecting weather outbreak information (740) for seasonal and non-seasonal changed predicted by data sources.

Figure 11:
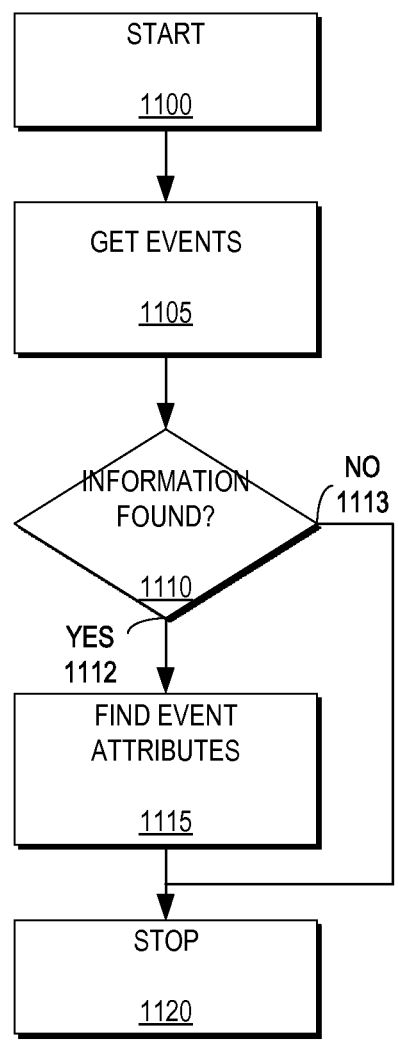

FIG. 11 is a flow diagram of a method according to an example embodiment of the present invention for determining events planned at a location at a time in the future. As illustrated in FIG. 11, the method starts (1100) and determines what events are planned for the given location at the time in the future (1105). Information may be found from a plurality of sources described above (1110). If information is found (1112), the method determines attributes of the event (1115), such as the duration, the number of expected attendees, and attributes of those attendees. Then method then stops (1120) and also stops if no information is found (1113).

Returning to FIG. 7, for each of the future event information (725), historic information (735), and weather information (745), if information is available (728), (738), (748), the method assigns a weighting to that information (750) and then calls the personalized alerts method (755) as described above with respect to FIG. 10. Similarly, if future, historic, and weather information are not available (727), (737), (747), the method also calls the personalized alerts method (755). The method then stops (760).

Figure 13:
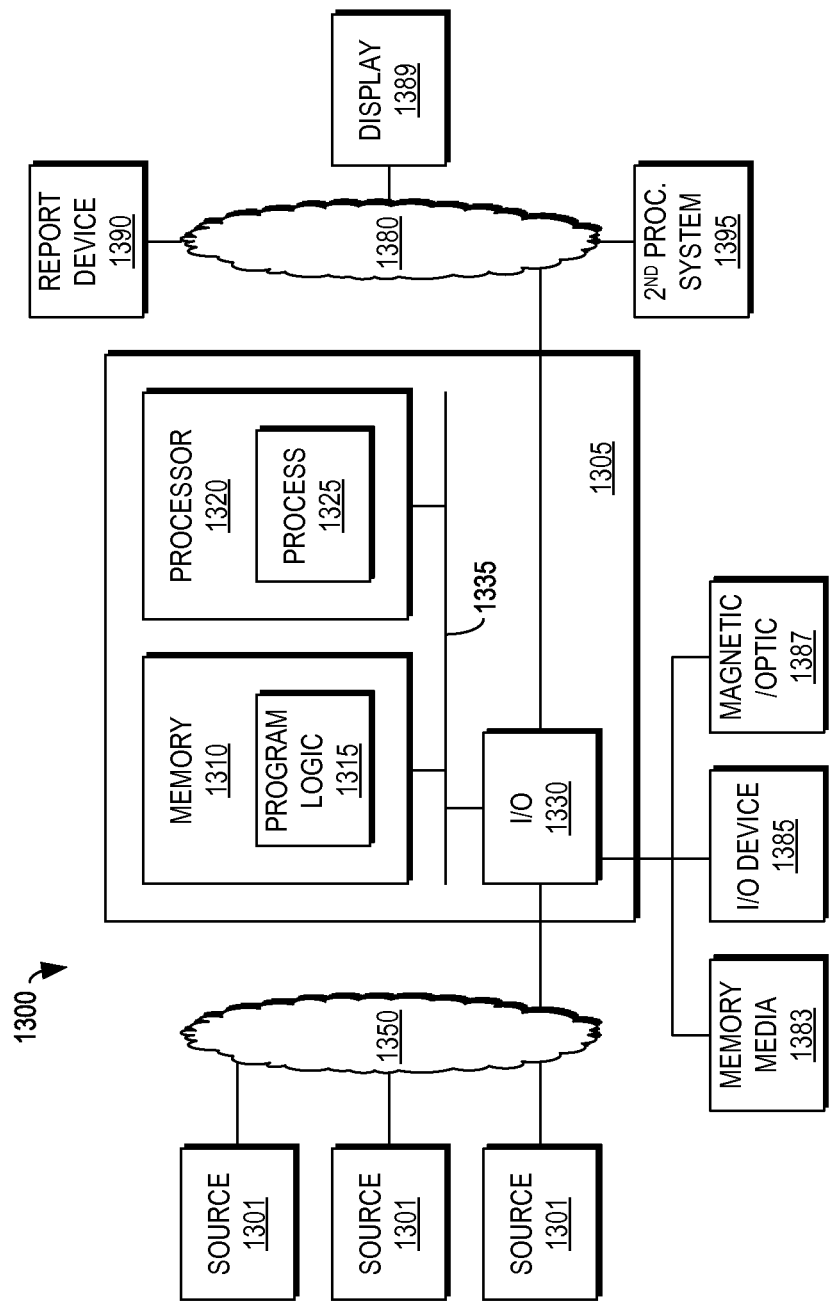
FIG. 13 is a block diagram of an apparatus according to an example embodiment of the present invention.

FIG. 13 is a block diagram of an example embodiment apparatus 1305 according to the present invention. The apparatus 1305 may be part of a system 1300 and includes memory 1310 storing program logic 1315, a processor 1320 for executing a process 1325, and a communications I/O interface 1330, connected via a bus 1335. The communications I/O interface 1330 is coupled with an input network 1350, output network 1380, memory media 1383, I/O device 1385, and magnetic/optic media 1387. In the example embodiment, the input network 1350 receives information from sources 1301, and the output network 1380 is coupled with a display 1389, a report device 1390, and a second processing system 1395.

The methods and apparatus of this invention may take the form, at least partially, of program code (i.e., instructions) embodied in tangible non-transitory media, such as floppy diskettes, CD-ROMs, hard drives, random access or read only-memory, or any other machine-readable storage medium. When the program code is loaded into and executed by a machine, such as the computer of FIG. 13, the machine becomes an apparatus for practicing the invention. When implemented on one or more general-purpose processors, the program code combines with such a processor to provide a unique apparatus that operates analogously to specific logic circuits. As such, a general purpose digital machine can be transformed into a special purpose digital machine.

Furthermore, it is to be appreciated that the processing apparatus 1305 of FIG. 13 may comprise virtual machines (VMs) implemented using a hypervisor. A hypervisor is an example of what is more generally referred to herein as "virtualization infrastructure." The hypervisor runs on physical infrastructure. As such, the data analytics and management techniques illustratively described herein can be provided in accordance with one or more cloud services. The cloud services thus run on respective ones of the virtual machines under the control of the hypervisor. Apparatus 1305 may also include multiple hypervisors, each running on its own physical infrastructure. Portions of that physical infrastructure might be virtualized.

As is known, virtual machines are logical processing elements that may be instantiated on one or more physical processing elements (e.g., servers, computers, processing devices). That is, a "virtual machine" generally refers to a software implementation of a machine (i.e., a computer) that executes programs like a physical machine. Thus, different virtual machines can run different operating systems and multiple applications on the same physical computer. Virtualization is implemented by the hypervisor which is directly inserted on top of the computer hardware in order to allocate hardware resources of the physical computer dynamically and transparently. The hypervisor affords the ability for multiple operating systems to run concurrently on a single physical computer and share hardware resources with each other.

An example of a commercially available hypervisor platform that may be used to implement portions of the apparatus 1305 in one or more embodiments of the invention is vSphere® by VMware, Inc. of Palo Alto, Calif. which may have an associated virtual infrastructure management system such as vCenter® by VMware. The underlying physical infrastructure may comprise one or more distributed processing platforms that include storage products such as VNX® and Symmetrix® VMAX®, both commercially available from EMC Corporation of Hopkinton, Mass. A variety of other computing and storage products may be utilized to implement the one or more cloud services that provide the entity location traceability and prediction functionality and features described herein.

Figure 14:
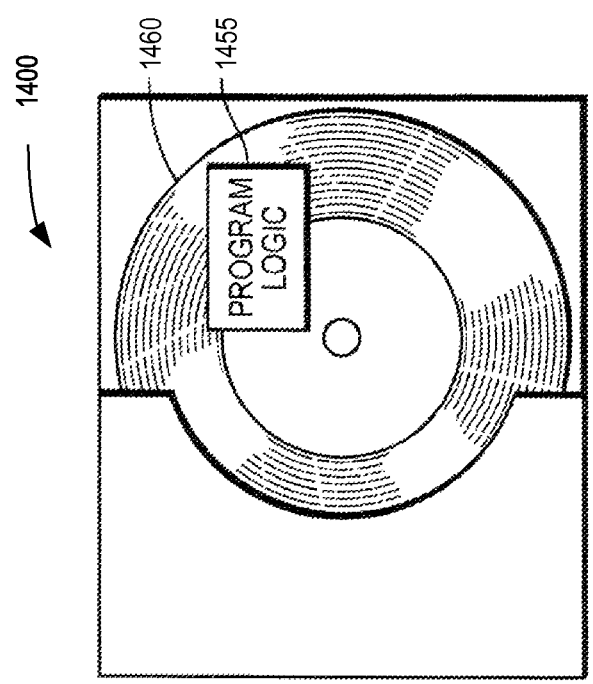
FIG. 14 is a diagram of a computer program product according to an example embodiment of the present invention.

FIG. 14 shows program logic 1455 embodied on a computer-readable medium 1460 as shown, and wherein the logic 1455 is encoded in computer-executable code configured for carrying out the methods of this invention, thereby forming a computer program product 1400.

The logic for carrying out the method may be embodied as part of the aforementioned system, which is useful for carrying out a method described with reference to embodiments shown. For purposes of illustrating the present invention, the invention is described as embodied in a specific configuration and using special logical arrangements, but one skilled in the art will appreciate that the device is not limited to the specific configuration but rather only by the claims included with this specification.

Consider a user registered with an example embodiment of the present invention who has made his medical and personal information available. The user may log in to an application embodiment the invention and search for disease outbreaks in location "locxyz" for the month of September 2013. According to a weather forecast for locxyc, it is going to be cloudy with a high chance of showers in the month of September. The user is going to attend the event "eventabc". Further, historic information is available for the month of September with information regarding a plurality of diseases (it should be noted that this information may continually be updated or added to).

First, the data collection module 130 may gather the data from a plurality of data sources 110 and, in combination with the ETL module 135, load the data into the data warehouse 140.

TABLE 5

Historic data

| Time period | Place | Event | Count | People affected | Disease | Weather Conditions | Comments |
|---|---|---|---|---|---|---|---|
| Sep-11 | Loc xyz | Event abc | 5000 | 100 | Meningococcal meningitis | Increases in temperature and decreases in humidity | 10 Women, 5 Men and 85 children were affected. |
| Sep-12 | Loc 123 | Event 123 | 8000 | 400 | Dengue, Malaria | High temperature, humidity and heavy rain | 260 Women, 40 Men and 100 children were affected. |

TABLE 6

Current data

| Time period | Place | People affected | Disease | Weather Conditions | Comments |
|---|---|---|---|---|---|
| September 2013 | locxyz | 10 | Meningococcal meningitis | Cloudy, rainfall expected | 10 Women, 5 Men and 85 children were affected. |
| September 2013 | Perth | 15 | Dengue | Extremely rainy | 10 Men, 5 Women were affected. |
| September 2013 | Allahabad | 35 | Typhoid | rainy | 15 kids, 10 men and 10 Women were affected. |

TABLE 7

Personalized data

| Time period | Place | People affected | Event | Weather Conditions | Comments |
|---|---|---|---|---|---|
| September 2013 | locxyz | NA | Eventabc | NA | NA |
| September 2013 | locxyz | NA | Eventabc | NA | NA |
| September 2013 | locxyz | NA | Eventabc | NA | NA |

The descriptive analytics module 262 then may transform the data into a list to push it into the predictive analytics module 264.

TABLE 8

Data in list for analysis

| | Time Period | Place | Weather Condition | Event | Count | People Affected |
|---|---|---|---|---|---|---|
| 1 | 3 | 1 | 5 | 0 | 8123 | 3064 |
| 2 | 2 | 2 | 12 | 10 | 8132 | 3291 |
| 3 | 5 | 3 | 5 | 11 | 7280 | 2695 |
| 4 | 5 | 4 | 17 | 0 | 7471 | 2721 |
| 5 | 2 | 5 | 0 | 6 | 8509 | 3328 |
| 6 | 5 | 6 | 5 | 5 | 8691 | 3144 |
| 7 | 2 | 7 | 6 | 5 | 8709 | 3225 |
| 8 | 7 | 8 | 12 | 5 | 8127 | 3011 |
| 9 | 4 | 9 | 4 | 8 | 8860 | 3390 |
| 10 | 22 | 10 | 4 | 0 | 7126 | 2812 |
| 11 | 20 | 11 | 5 | 0 | 8182 | 3250 |
| 12 | 19 | 12 | 18 | 5 | 8261 | 3250 |
| 13 | 8 | 13 | 22 | 10 | 8265 | 3248 |
| 14 | 8 | 14 | 6 | 12 | 8146 | 3185 |
| 15 | 4 | 15 | 6 | 13 | 8210 | 3174 |
| 16 | 17 | 16 | 0 | 12 | 7675 | 3194 |
| 17 | 8 | 17 | 4 | 6 | 8124 | 3252 |
| 18 | 2 | 18 | 5 | 10 | 8710 | 3378 |
| 19 | 5 | 19 | 4 | 10 | 7095 | 2360 |
| 20 | 53 | 20 | 5 | 10 | 8270 | 3284 |
| 21 | 2 | 21 | 0 | 0 | 7642 | 3017 |
| 22 | 4 | 22 | 0 | 0 | 7089 | 3378 |
| 23 | 2 | 23 | 0 | 5 | 6356 | 2286 |
| 24 | 24 | 24 | 0 | 10 | 7701 | 2981 |
| 25 | 1 | 25 | 14 | 5 | 7785 | 3096 |
| 26 | 25 | 26 | 10 | 10 | 7888 | 3282 |
| 27 | 1 | 27 | 0 | 10 | 7949 | 3008 |
| 28 | 2 | 28 | 14 | 5 | 6866 | 2380 |
| 29 | 3 | 29 | 0 | 7 | 7708 | 3076 |
| 30 | 19 | 30 | 0 | 0 | 8734 | 3588 |
| 31 | 0 | 31 | 0 | 10 | 8457 | 3345 |
| 32 | 10 | 32 | 0 | 5 | 7734 | 3051 |
| 33 | 4 | 33 | 4 | 0 | 7982 | 2996 |
| 34 | 3 | 34 | 6 | 0 | 7528 | 2903 |
| 35 | 4 | 35 | 9 | 17 | 8549 | 3409 |
| 36 | 47 | 36 | 0 | 0 | 7674 | 2855 |
| 37 | 0 | 37 | 4 | 10 | 7058 | 2823 |
| 38 | 2 | 38 | 18 | 5 | 7779 | 3065 |
| 39 | 28 | 39 | 0 | 0 | 7691 | 3139 |
| 40 | 4 | 40 | 4 | 5 | 7992 | 3030 |
| 41 | 0 | 41 | 10 | 0 | 7697 | 2964 |
| 42 | 1 | 42 | 9 | 15 | 7712 | 3028 |
| 43 | 15 | 43 | 5 | 0 | 8097 | 3049 |
| 44 | 3 | 44 | 0 | 5 | 8381 | 3217 |
| 45 | 3 | 45 | 12 | 10 | 7456 | 3244 |
| 46 | 10 | 46 | 6 | 0 | 7684 | 3211 |
| 47 | 46 | 47 | 4 | 0 | 6322 | 2561 |
| 48 | 18 | 48 | 6 | 6 | 7877 | 3157 |
| 49 | 1 | 49 | 4 | 5 | 7609 | 3218 |
| 50 | 1 | 50 | 4 | 17 | 8226 | 3276 |

The predictive analytics module 264 then may perform a correlation on the data pushed in the analytical model to determine a correlation matrix as an output for each disease in the data 245 provided from the data warehouse 240. The correlation matrix allots a correlation value "r" to every attribute for every disease.

Based upon the correlation value "r", example embodiments of the present invention assign the weightage to the attributes for every disease. For example, for each disease of a plurality of diseases (e.g., Malaria, Meningococcal, Meningitis, Dengue, and Typhoid), a correlation matrix is generated for each disease. The mean of the "r" values for historical values is then calculated (according to the data of Table 1) as:

$$rHist=[1.00+0.13+(-0.11)+0.14+(-0.04)+0.02]/6=0.19.$$

Similarly, rHist, rCur, and rPers are calculated for all attributes (i.e., Place, Weather.Condition, Event, Count, and People Affected).

The weighting for each disease is then assigned.

For example, for Malaria:

$$D1=[W1+W2+W3+W4+W5+W6]=[10+7+7+6+8+9]=47; \text{ and}$$

$$\text{Mean}(D1)=[10+7+7+6+8+9]/6=7.833\approx8.$$

Similarly, Meningococcal:

$$\text{Mean}(D2)=[6+8+7+7+6+5]/6=6.5\approx7,$$

for Meningitis:

$$\text{Mean}(D3)=[5+5+7+7+6+5]/6=5.833\approx6,$$

for Dengue:

$$\text{Mean}(D4)=[5+6+8+7+6+6]/6=6.33\approx6, \text{ and}$$

for Typhoid:

$$\text{Mean}(D5)=[8+7+7+5+6+5]/6=6.33\approx6.$$

The mean weight for the set of diseases is:

$$\text{Mean}([D1,D2,D3,D4,D5])=[8+7+7+6+6]=6.8,$$

with a standard deviation of:

$$SD([D1,D2,D3,D4,D5])=0.83666.$$

Therefore, the Z-scores for each disease may be calculated as:

$$Z1(D1)=[8-6.8]/0.83666=1.4342,$$

$$Z2(D2)=[7-6.8]/0.83666=0.2390,$$

$$Z3(D3)=[7-6.8]/0.83666=0.2390,$$

$$Z4(D4)=[6-6.8]/0.83666=(-0.9561), \text{ and}$$

$$Z5(D5)=[6-6.8]/0.83666=(-0.9561).$$

Sorting the list of Z-scores in descending, including eliminating ties between D2 and D3 and D4 and D5, respectively, yields Z1 (Malaria) as the disease with the greatest chance of outbreak in the month of September 2013.

TABLE 9

Disease ranking

| Rank | Disease |
|---|---|
| 1 | Malaria (D1) |
| 2 | Meningococcal (D2) |
| 3 | Meningitis (D3) |
| 4 | Dengue (D4) |
| 5 | Typhoid (D5) |

Although the foregoing invention has been described in some detail for purposes of clarity of understanding, it will be apparent that certain changes and modifications may be practiced within the scope of the appended claims. Accordingly, the present implementations are to be considered as illustrative and not restrictive, and the invention is not to be limited to the details given herein, but may be modified within the scope and equivalents of the appended claims.

What is claimed is:

1. A method comprising:
receiving a request from a given user to predict disease outbreak information for a given location and a given time;
obtaining, from a plurality of data sources, a first set of disease outbreak patterns for the given location and the given time;
assigning weights to one or more reported diseases in the first set of disease outbreak patterns for the given location, the weights being based at least in part on an authenticity of one or more of the plurality of data sources from which data regarding the one or more reported diseases is obtained;
obtaining a second set of disease outbreak patterns for the given location at one or more historic time periods;
assigning weights to one or more reported diseases in the second set of disease outbreak patterns based at least in part on determining whether data in the second set of disease outbreak patterns correlates with data in the first set of disease outbreak patterns;
obtaining a set of personalized trends for the given user;
assigning weights to the set of personalized trends based at least in part on determining whether user profile attributes in the set of personalized trends correlate with the first set of disease outbreak patterns and the second set of disease outbreak patterns; and
generating at least one personalized alert for the given user based on the assigned weights for the first set of disease outbreak patterns, the second set of disease outbreak patterns, and the set of personalized trends; and
delivering the at least one personalized alert to a computing device associated with the given user over at least one network;
wherein the method is performed by at least one processing device comprising a processor coupled to a memory.

2. The method of claim 1 wherein the given location comprises a current location of the given user and the given time comprises a current time, and further comprising determining the current location of the given user by identifying a communication channel utilized by the given user and utilizing the identified communication channel to obtain information for determining the current location of the given user.

3. The method of claim 2 wherein the identified communication channel comprises communication via the computing device, wherein the computing device comprises a mobile computing device, and wherein utilizing the identified communication channel to obtain the information for determining the current location of the given user comprises utilizing at least one of global positioning system data and mobile network data of the mobile computing device to determine the current location of the given user.

4. The method of claim 2 wherein the identified communication channel comprises communication via the computing device over an Internet Protocol network, and wherein utilizing the identified communication channel to obtain the information for determining the current location of the given user comprises utilizing an Internet Protocol network address of the computing device.

5. The method of claim 2 wherein the identified communication channel comprises communication via the computing device, and wherein utilizing the identified communication channel to obtain the information for determining the current location of the given user comprises utilizing at least one calendar application running on the computing device to determine the current location of the given user.

6. The method of claim 2 wherein obtaining the first set of disease outbreak patterns comprises:
checking the plurality of data sources for data regarding current disease outbreak patterns for one or more of the reported diseases, the plurality of data sources comprising two or more of a health sector data source, a news data source, and a social medial data source;
for each of the plurality of data sources, determining whether data from that data source is newer than a predefined threshold for stale data;
utilizing the data from each of the plurality of data sources determined to be newer than the predefined threshold for stale data to calculate the first set of disease outbreak patterns.

7. The method of claim 1 wherein obtaining the second set of disease outbreak patterns comprises:
determining whether historical disease outbreak information for one or more of the reported diseases is available for the given location in the one or more historic time periods; and
for each of the one or more reported diseases for which the historical disease outbreak information is available, identifying a number of unique reports of that reported disease and patient details for each of the unique reports of that reported disease.

8. The method of claim 7 wherein obtaining the second set of disease outbreak patterns further comprises:
checking for one or more historical disease outbreak events at the given location in the one or more historic time periods; and
for each of the one or more historical disease outbreak events at the given location in the one or more historic time periods, identifying a number of people in attendance at that historical disease outbreak event and patient details for each of the people in attendance at that historical disease outbreak event.

9. The method of claim 1 wherein obtaining the set of personalized trends for the given user comprises:
obtaining a user profile for the given user, the user profile comprising available health record information for the given user;
obtaining user profiles comprising available health record information for one or more companion users responsive to determining that the given user is associated with the one or more companion users at the given time;
determining a set of one or more additional users at the given location at the given time having associated user profiles matching at least one of the user profile for the given user and a user profile for one or more of the companion users;
obtaining social media data from one or more social media data sources for the given user, the one or more companion users and the one or more additional users; and
capturing travel context of the given user based at least in part on the user profiles and obtained social media data for the given user, the one or more companion users and the one or more additional users.

10. The method of claim 1 wherein the personalized alert comprises one or more real-time location-aware recommendations for one or more medical care centers near the given location.

11. The method of claim 10 wherein the one or more medical care centers near to the given location are selected based at least in part on one or more user-specific recommendations associated with past medical conditions of the given user and health care providers previously utilized by the given user.

12. The method of claim 1 wherein the personalized alert comprises one or more real-time intelligent recommendations for precautionary measures to handle one or more expected medical conditions of one or more of the reported diseases in the first set of disease outbreak patterns.

13. The method of claim 1 wherein the given location comprises a future location of the given user, and wherein obtaining the first set of disease outbreak patterns comprises identifying one or more events planned for the future location at the given time and determining attributes of the one or more events planned for the future location at the given time, the attributes comprising a duration, a number of expected attendees and attributes of the expected attendees for the one or more events.

14. The method of claim 13 wherein obtaining the first set of disease outbreak patterns further comprises determining weather information for identifying seasonal and non-seasonal changes predicted by the plurality of data sources for the future location at the given time.

15. An apparatus comprising:
at least one processing device comprising a processor coupled to a memory;
the at least one processing device being configured:
to receive a request from a given user to predict disease outbreak information for a given location and a given time;
to obtain, from a plurality of data sources, a first set of disease outbreak patterns for the given location and the given time;
to assign weights to one or more reported diseases in the first set of disease outbreak patterns for the given location, the weights being based at least in part on an authenticity of one or more of the plurality of data sources from which data regarding the one or more reported diseases is obtained;
to obtain a second set of disease outbreak patterns for the given location at one or more historic time periods;
to assign weights to one or more reported diseases in the second set of disease outbreak patterns based at least in part on determining whether data in the second set of disease outbreak patterns correlates with data in the first set of disease outbreak patterns;
to obtain a set of personalized trends for the given user;
to assign weights to the set of personalized trends based at least in part on determining whether user profile attributes in the set of personalized trends correlate with the first set of disease outbreak patterns and the second set of disease outbreak patterns; and
to generate at least one personalized alert for the given user based on the assigned weights for the first set of disease outbreak patterns, the second set of disease outbreak patterns, and the set of personalized trends; and
to deliver the at least one personalized alert to a computing device associated with the given user over at least one network.

16. The apparatus of claim 15 wherein the given location comprises a current location of the given user and the given time comprises a current time, and wherein the at least one processing device is further configured to determine the current location of the given user by identifying a communication channel utilized by the given user and utilizing the identified communication channel to obtain information for determining the current location of the given user.

17. The apparatus of claim 15 wherein the given location comprises a future location of the given user, and wherein obtaining the first set of disease outbreak patterns comprises identifying one or more events planned for the future location at the given time and determining attributes of the one or more events planned for the future location at the given time, the attributes comprising a duration, a number of expected attendees and attributes of the expected attendees for the one or more events.

18. A computer program product comprising a non-transitory processor-readable storage medium having stored therein program code of one or more software programs, wherein the program code when executed by at least one processing device causes the at least one processing device:

- to receive a request from a given user to predict disease outbreak information for a given location and a given time;
- to obtain, from a plurality of data sources, a first set of disease outbreak patterns for the given location and the given time;
- to assign weights to one or more reported diseases in the first set of disease outbreak patterns for the given location, the weights being based at least in part on an authenticity of one or more of the plurality of data sources from which data regarding the one or more reported diseases is obtained;
- to obtain a second set of disease outbreak patterns for the given location at one or more historic time periods;
- to assign weights to one or more reported diseases in the second set of disease outbreak patterns based at least in part on determining whether data in the second set of disease outbreak patterns correlates with data in the first set of disease outbreak patterns;
- to obtain a set of personalized trends for the given user;
- to assign weights to the set of personalized trends based at least in part on determining whether user profile attributes in the set of personalized trends correlate with the first set of disease outbreak patterns and the second set of disease outbreak patterns; and
- to generate at least one personalized alert for the given user based on the assigned weights for the first set of disease outbreak patterns, the second set of disease outbreak patterns, and the set of personalized trends; and
- to deliver the at least one personalized alert to a computing device associated with the given user over at least one network.

19. The computer program product of claim 18 wherein the given location comprises a current location of the given user and the given time comprises a current time, and wherein the program code when executed further causes at least one processing device to determine the current location of the given user by identifying a communication channel utilized by the given user and utilizing the identified communication channel to obtain information for determining the current location of the given user.

20. The computer program product of claim 18 wherein the given location comprises a future location of the given user, and wherein obtaining the first set of disease outbreak patterns comprises identifying one or more events planned for the future location at the given time and determining attributes of the one or more events planned for the future location at the given time, the attributes comprising a duration, a number of expected attendees and attributes of the expected attendees for the one or more events.

* * * * *